(12) United States Patent
Gianolio et al.

(10) Patent No.: US 7,387,836 B2
(45) Date of Patent: Jun. 17, 2008

(54) AZIRIDINE COMPOUNDS AND THEIR USE IN MEDICAL DEVICES

(75) Inventors: Diego A. Gianolio, Boston, MA (US); Erika E. Johnston, Cambridge, MA (US); Robert J. Miller, E. Bridgewater, MA (US)

(73) Assignee: Genzyme Corporation, Cambridge, MA (US)

( * ) Notice: Subject to any disclaimer, the term of this patent is extended or adjusted under 35 U.S.C. 154(b) by 504 days.

(21) Appl. No.: 10/511,425

(22) PCT Filed: Apr. 17, 2003

(86) PCT No.: PCT/US03/12139

§ 371 (c)(1), (2), (4) Date: May 4, 2005

(87) PCT Pub. No.: WO03/089026

PCT Pub. Date: Oct. 30, 2003

(65) Prior Publication Data

US 2005/0249953 A1    Nov. 10, 2005

(51) Int. Cl.
*B05D 5/00* (2006.01)
*C08F 2/34* (2006.01)
*C08F 2/52* (2006.01)
*C08J 7/18* (2006.01)
*B32B 9/00* (2006.01)

(52) U.S. Cl. .................. 428/411.1; 427/488; 427/491; 427/2.13; 427/2.31

(58) Field of Classification Search .................. None
See application file for complete search history.

(56) References Cited

U.S. PATENT DOCUMENTS

| | | | |
|---|---|---|---|
| 3,338,885 A | | 8/1967 | Coker et al. |
| 3,828,024 A | | 8/1974 | Breslow |
| 5,057,371 A | * | 10/1991 | Canty et al. .............. 428/411.1 |
| 5,153,113 A | * | 10/1992 | Hirabayashi et al. ........ 430/522 |
| 5,280,084 A | | 1/1994 | Paul |
| 5,599,576 A | | 2/1997 | Opolski |
| 6,221,425 B1 | * | 4/2001 | Michal et al. .............. 427/2.25 |
| 6,231,600 B1 | | 5/2001 | Zhong |
| 6,248,127 B1 | * | 6/2001 | Shah et al. ................. 623/1.15 |
| 6,361,819 B1 | * | 3/2002 | Tedeschi et al. ............ 427/2.24 |
| 2001/0000785 A1 | | 5/2001 | Opolski |
| 2001/0034336 A1 | | 10/2001 | Wolfgang et al. |

FOREIGN PATENT DOCUMENTS

| | | | |
|---|---|---|---|
| DE | 1270287 | | 6/1968 |
| DE | 1243687 | | 7/1997 |
| FR | 1455085 | | 10/1996 |
| GB | 2151244 | | 7/1985 |
| GB | 2151246 | | 1/1987 |
| JP | 64-17071 | * | 1/1989 |
| NL | 6504747 | | 10/1996 |
| SU | 1723125 | | 3/1992 |

OTHER PUBLICATIONS

W. McCoull et al., "Recent Synthetic Applications of Chiral Aziridines", *Synthesis* 2000, No. 10, pp. 1347-1365 (2000), no month.
R. D'Agostino, "PE-CVD of Polymer Films: Mechanisms, Chemistry, and Diagnosis", pp. 3-46 (1997), no month.
P. Andersson et al., "Enantioselective Addition of Organolithium Reagents toImines Mediated by $C_2$-Symmetric Bis(aziridine) Ligands", *Tetrahedron* 54, pp. 11549-11566 (1998), no month.
D. Tanner, et al., "Asymmetric Catalysis via Chiral Aziridines", *Acta Chemica Scandinavia*, vol. 50, No. 4, pp. 361-368 (1996), no month.
Denmark et al., "Preparation of Chiral Bisoxazolines: Observations on the Effect of Substituents", *J. Org. Chem.*, vol. 60, pp. 4884-4892 (1995).
Kadorkina et al., Izv. Akad. Nauk SSSR Ser. Khim. 4, pp. 882-885 (1991) Abstract -English, no month.
G. Manecke, et al., "Amphotere ion exchanger", *Die Makromolekulare Chemie*, vol. 175, pp. 1833-1845 (1974), no month with English abstract.
Watanabe et al., "Synthesis of Aziridine Derivatives from Unsaturated Carboxylic Acid Halides or Chloroformates and Aziridine", *Kogyo Kagaku Zasshi*, vol. 72 (6) pp. 1349-1352 (1969), no month with English abstract.

* cited by examiner

*Primary Examiner*—Marianne Padgett
(74) *Attorney, Agent, or Firm*—Cohen Pontani Lieberman & Pavane LLP

(57) ABSTRACT

There are disclosed novel uses of aziridine compounds. The aziridine compounds can be formed into films by plasma deposition on a wide variety of substrates. The films prevent biofouling, impart biocompatible or antithrombotic properties, and can immobilize therapeutic and pharmaceutical agents to provide a drug delivery system.

52 Claims, No Drawings

AZIRIDINE COMPOUNDS AND THEIR USE IN MEDICAL DEVICES

BACKGROUND OF THE INVENTION

1. Field of the Invention

This invention is directed to novel uses of and products from aziridine compounds. More particularly, this invention is directed to plasma-deposited aziridine compounds in the form of a film. The film can be used to prevent biofouling or to immobilize a therapeutic agent. Even more particularly, this invention is directed to the use of such films in time release pharmaceutical compositions.

2. Description of the Related Art

It is known how to synthesize a variety of aziridine compounds using different methodologies. The use of aziridine compounds as inhibitors of aluminum corrosion and as biomedical agents are also known.

For example, W. McCoull, et al. (*Synthesis* 2000, No, 10, 1347-1365) disclose a summary of the use of chiral aziridines in synthesis emphasizing the effect of various substituents on ring openings, rearrangements and the use of chiral ligands and auxiliaries.

Netherlands Patent Application 19,650,414 discloses aziridinyl compounds that are useful as inhibitors of aluminum corrosion by halogenated hydrocarbons.

French Patent Application 19,650,413 discloses aziridinyl compounds that are useful as inhibitors of aluminum decomposition by halogenated degreasing agents and as inhibitors of the growth of *Escherichia coli*.

U.S. Pat. No. 3,338,885 to Coker, et. al. discloses (1-aziridinyl) alkyl esters of carboxylic acids and (1-aziridinyl) alkanols that are useful as inhibitors of aluminum reaction with halogenated degreasing solvents.

There has been, however, no previous teaching that aziridine compounds may form films or coatings by plasma deposition on a variety of substrates

SUMMARY OF THE INVENTION

It has now been found that aziridine compounds can be formed into films by plasma deposition on a wide variety of substrates. The films prevent biofouling, impart biocompatible or antithrombotic properties, and can immobilize therapeutic and pharmaceutical agents to provide a drug delivery system.

In general, the invention is directed to a process of producing a coated surface on a substrate by plasma depositing an aziridine compound onto the substrate to produce at least one aziridine coated surface on the substrate.

The substrate may be generally any compatible material, including polyethylene terephthalate, polycarbonate, polymethacrylate, silicone, polytetrafluoroethylene, polyurethanes, polybutadienes, epoxies, polystyrenes, polybutyrates, hydroxy apatites, ceramics, glass, and metals, such as stainless steel, nitinol, and titanium. The substrate is preferably cleaned by, for instance, etching with oxygen before the plasma deposition of the aziridine compound.

The aziridine compound may have at least one functional group attached to the aziridine that is susceptible to fragmentation and recombination, with the proviso that the functional group is not silane or siloxane, and, if the nitrogen atom of the aziridine is attached to hydrogen, then an alkyl pendant to the carbon of the aziridine has 4 or more carbon atoms.

Generally, when 'monomer' molecules, such as aziridine compounds having a least one functional group, enter a plasma reactor it suffers collisions with electrons and then produces fragments of the functional group to some extent. These reactive species lead to the formation and recombination of new gas phase compounds, which can also lead to new reactive fragments. The reactive species can be regarded as the "building blocks" for the construction of thin polymeric films." See D'Agostino, R. 'PE-CVD of Polymer Films: Mechanisms, Chemistry, and Diagnostics' in Plasma Processing of Polymers, edited by R. d'Agostino, P. Favia, and F. Fracassi. NATO ASI Series E, Applied Sciences, Vol. 346, p3-46.

The functional group may be selected from the group consisting of alkyl, allyl, alkoxy, alkylene, aryl, ester, ether, ethylene glycol, oligoethylene glycol, and acryl.

Preferably, the aziridine compound has a molecular weight of 600 or less so as to have sufficient vapor pressure for use in plasma deposition. It is preferred that the aziridine compound form radical ions during plasma deposition to facilitate the formation of the aziridine film on to a substrate. In one embodiment of the present invention, the aziridine is linked to an acryl group by a linker selected from the group consisting of alkyl, alkylene, alkylene oxide, alkyl diols, and combinations thereof. The linker may be combination of both. One preferable aziridine compound for plasma deposition is 2-(1-aziridinyl) ethyl methacrylate.

More specifically, the aziridine compound has preferably the following Formulas I, II and III.

(I)

wherein $R_1$ is selected from the group consisting of a substituted or unsubstituted alkyl, alkoxy, alkenyl, alkinyl, aryl, arylalkyl, cycloalkylalkyl, cycloalkenyl, heterocyclic, heteroaryl, heteroarylalkyl, acrylate, alkylacrylate, alkylacrylate esters, alkylester, alkylether, alkylcarbonyl, fluorocarbon, ethylene glycol, oligo ethylene glycol groups, and combinations thereof.

(II)

wherein $R_2$ is selected from the group consisting of a substituted or unsubstituted alkyl having 4 or more carbon atoms, alkoxy, alkenyl, alkinyl, aryl, arylalkyl, cycloalkylalkyl, cycloalkenyl, heterocyclic, heteroaryl, heteroarylalkyl, acrylate, alkylacrylate, alkylacrylate esters, alkylester, alkylether, alkylcarbonyl, fluorocarbon, ethylene glycol, oligo ethylene glycol groups, and combinations thereof.

(III)

wherein $R_1$ and $R_3$ are selected from the group consisting of a substituted or unsubstituted alkyl, alkoxy, alkenyl, alkinyl, aryl, arylalkyl, cycloalkylalkyl, cycloalkenyl, heterocyclic, heteroaryl, heteroarylalkyl, acrylate, alkylacrylate, alkylacrylate esters, alkylester, alkylether, alkylcarbonyl, fluorocarbon, ethylene glycol, oligo ethylene glycol groups, and combinations thereof.

For the above aziridine compounds of Formulas I, II and III, the substitution group may be a halogen, $C_1$-$C_{22}$ alkyl, nitro, cyano, aryl, thiol, cycloalkyl, fluorocarbon, ethylene glycol, oligoethylene glycol or heterocyclic group.

For the purposes of the present invention, the term "alkyl" refers to a straight chain or branched saturated hydrocarbyl group. Preferred alkyl groups include $C_1$-$C_{22}$-alkyl groups, while more preferred alkyl groups include $C_1$-$C_{14}$-alkyl groups unless otherwise specified.

The term "cycloalkyl" refers to a mono-, bi- or polycyclic alkyl group. Preferred cycloalkyl groups include $C_3$-$C_8$-cycloalkyl groups.

The term "alkoxy" refers to an alkyl-O— group or a cycloalkyl-O— group, where the preferred alkyl and cycloalkyl groups are those given above.

The term "alkenyl" refers to a straight chain or branched hydrocarbyl group which includes one or more The term "cycloalkenyl" refers to a cyclic hydrocarbyl group which includes one or more double bonds but is not aromatic. Preferred cycloalkenyl groups include $C_5$-$C_8$-cycloalkenyl groups.

The term "aryl" refers to an aromatic carbocyclic group, such as a phenyl group, a naphthyl group or a phenyl or naphthyl group which is fused with a five or six-membered saturated, partially unsaturated or aromatic carbocyclic or heterocyclic ring.

The terms "heterocycle" and "heterocyclic group" refer to a saturated, aromatic or partially unsaturated ring system which includes at least one heteroatom, such as one or more oxygen, nitrogen or sulfur atoms or a combination thereof. Saturated heterocyclic groups ("heterocycloalkyl groups") include piperidyl, pyrollidyl, piperazyl tetrahydrofuranyl and morpholyl.

The term "heteroaryl" refers to an aromatic heterocyclic group. Suitable heteroaryl groups include, but are not limited to, pyridyl, pyrimidyl, quinolyl, isoquinolyl, pyrrolyl, quinoxalyl, imidazolyl, oxazolyl, isoxazolyl, pyrazolyl, thienyl, furanyl, pyrazolyl, thiadiazolyl, oxadiazolyl, indazolyl, thiazolyl, isothiazolyl, and tetrazolyl. Heteroaryl groups also include ring systems in which a carbocyclic aromatic ring, carbocyclic non-aromatic ring or heteroaryl ring is fused to one or more other heteroaryl rings (e.g., benzo(b)thienyl, benzimidazolyl, benzoxazolyl, benzothiazolyl, benzothiadiazolyl, benzoxadiazolyl, indolyl, tetrahydroindolyl, azaindolyl, indazolyl, quinolinyl, imidazopyridyl, puryl, pyrrolo[2,3-d]pyrimidyl, pyrazolo[3,4-d]pyrimidyl).

The term "arylalkyl" refers to an alkyl group which is substituted by one or more substituted or unsubstituted aryl groups. Preferred arylalkyl groups include benzyl, diphenylmethyl and 2-phenethyl groups.

The term "heteroarylalkyl" refers to an alkyl group which is substituted by a substituted or unsubstituted heteroaryl group.

The term "acrylate" refers to a functional group that contains substituted or unsubstituted conjugated ester bonds.

The term "ester" refers to a substituted or unsubstituted functional group that contains the structure C—C(=O)—O.

The term "ether" refers to substituted or unsubstituted functional group that contains the structure C—O—C.

The term "carbonyl" refers to a substituted or unsubstituted functional group that contains the structure C=O.

The process of plasma deposition may further include the step of coating the aziridine coated surface with a biopolymer, such as a protein, heparin complex, polysaccharide, phosphonic acid, and nucleic acid. The polysaccharide may be, but is not limited to, hyaluronan, alginate, or carboxymethyl cellulose. The protein may be, but is not limited to, collagen, laminin or albumin. The nucleic acid may be, but is not limited to, DNA, RNA or antisense material. Furthermore, blood compatibility may be also imparted by exposing the aziridine surface to blood which in turn will result in the covalent deposition of blood proteins onto the surface. Adherence of serum albumin would passivate the surface to further thrombus formation through the binding and activation of fibrinogen.

The process of the present invention provides a device having a plasma deposited film of an aziridine compound on at least a portion of its surface. The film is capable of preventing biofouling, such as cell and platelet adhesion when the device is in contact with blood, plasma or tissue. The film may also impart biocompatible or antithrombotic properties to the device. If a pharmaceutical or therapeutic agent is immobilized onto the film, the device may be used as a controlled release drug delivery system.

The pharmaceutical or therapeutic agent includes, but is not limited to, anti-allergenics, anti-bacterials, anti-virals, anti-fungals, anti-inflammatories, antiplatelets, antithrombotics, anesthetics, anti-proliferatives, genetic materials and mixtures thereof. The genetic materials may be, but is not limited to, DNA, RNA and antisense material.

Alternatively, the aziridine film on the device may be covered by a biopolymer layer. The biopolymer may be, but is not limited to, protein, heparin complex, polysaccharide, phosphonic acid, and nucleic acid. Preferably, the polysaccharide is hyaluronan. In one embodiment, a pharmaceutical or therapeutic agent is immobilized onto the biopolymer layer.

The present invention additionally provides a method of preventing cell adhesion on a substrate by the application of an aziridine film on the substrate. This method may further include the application of a biopolymer layer onto the aziridine film. Suitable biopolymers are those discussed above.

The various features of novelty that characterize the invention are pointed out with particularity in the claims annexed to and forming a part of the disclosure. For a better understanding of the invention, its operating advantages, and specific objects attained by its use, reference should be had to the descriptive matter in which there are illustrated and described preferred embodiments of the invention.

DETAILED DESCRIPTION OF THE PRESENTLY PREFERRED EMBODIMENTS

Single or multi-layer coatings are provided herein that are designed to impart thromboresistance and/or biocompatibility to a medical device or provide a drug delivery system.

The first coating of the present invention initially is a plasma-deposited film formed from a compound having an aziridine functional group. The compound may further have groups such as alkyl, allyl, alkoxy, alkylene, aryl, ester, ether, ethylene glycol, oligoethylene glycol, and acryl. The aziridine compound may contain more than one aziridine functional group. Useful aziridine compounds include, but are not limited to, diaziridines such as di[2-(1-aziridinyl)ethyl)]adipate, pentaerythritol tris(3-aziridinopropionate), discussed in GB 2,151,244 and 2,151,246 of Balazs et al.; 1,3-bis(1-aziridinyl)-3-phenyl-1-propanol; 1,1'-(1,3-propanediyl)bis-2-aziridinecarbonitrile, discussed in German Patent DE 2163623; α, β-bis(1-aziridinyl) 2-furanpropanol; 1-[3-(1-aziridinyl)propionyl]-aziridine; 1,3-bis(1-aziridinyl)-2-propanol; 1,3-bis(2-methyl-1-aziridinyl)-2-propanol; (1-aziridinylpyruvoyl)-, 1-[(p-nitrophenyl)hydrazone] aziridine; 1,1'-

(1,3-dioxo-1,3-propanediyl) bis-aziridine, and those diaziridines disclosed in Andersson et al., Tetrahedron 54(38), 11549 (1998); Tanner et al., Acta Chem. Scand. 50(4), 361 (1996); Olivier et al., J. Org. Chem. 60(15), 4884 (1995); Russian Patent SU 1723125 (bisaziridine alkanes); Kadorkina et al., Izv. Akad. Nauk SSSR, Ser. Khim. 4, 882 (1991); Manecke et al., Makromol. Chem. 175(6), 1833 (1974); Manecke et. al. German Patent DE 1270287; Watanabe et al., Kogyo Kagaku Zasshi 72(6), 1349 (1969); and Hillers et al.; Bestian et al., German Patent DE 1243687.

The molecular weight of the aziridine compound must be low enough to allow for the vaporization of the compound during plasma deposition. Preferably, the molecular weight is not more than 600.

Coatings of the present invention may be applied to medical devices that are placed in the human body, or that remain outside the body. Coated medical devices that are placed in the human body may include stents, cathethers, needles, prostheses, surgical assist devices, picc lines and other devices. Coated medical devices that remain outside the human body may include tubing for the transport of blood and vessels for the storage of blood, dialysis filters, oxygenation membranes, and blood filters. Substrates or medical devices on which the coatings described herein may be applied can include a wide variety of materials, including stainless steel, nitinol, tantalum, glass, ceramics, nickel, titanium, aluminum and other materials suitable for manufacture of a medical device.

The coatings disclosed herein may further include a film-forming agent for the aziridine coating. The film forming-agent could be added in a second layer. For example, the aziridine coating comprising aziridine functionality may be chemically linked to a biopolymer as a second layer that provides anti-thrombogenicity or biocompatibility. The biopolymer may be selected from a group of proteins, heparin complexes, polysaccharides, phosphonic acids, and nucleic acids. Polysaccharides include, but are not limited to, hyaluronan, alginate, and carboxymethyl cellulose. Appropriate film-forming agents could also include cellulose esters, polydialkyl siloxanes, polyurethanes, acrylic polymers or elastomers, as well as biodegradable polymers such as polylactic acid (PLA), polyglycolic acid (PGA), copolymers of PLA and PGA, known as PLGA, poly($\epsilon$-caprolactone), and the like.

Various methods of making the second layer of the present invention are possible, and examples of such methods and certain resulting coatings are as follows. Such methods and coatings are disclosed by way of example, and are not intended to be limiting, as other examples may be readily envisioned by one of ordinary skill in the art. The following examples include methods of providing coatings of the present invention in a single layer having the aziridine compound, with and without the need for a second layer. In some instances, experimental results are provided showing sustained bioactivity for a particular coating.

The second layer can be applied in a wide variety of conventional ways, including painting, spraying, dipping, vapor deposition, epitaxial growth and other methods known to those of ordinary skill in the art.

Coatings, derived from the above-described methods, on coupons were tested in various ways. First, as a qualitative test, coupons coated with an aziridine first layer alone were dipped in rhodamine B solution and then were screened for the presence of a pink stain.

The presence of a pink stain indicates the presence of reaction between aziridine and rhodamine B in the sample being assayed. Additionally, the intensity of the color observed in this assay is proportional to the amount of aziridine in the sample. Therefore, a comparison of the intensities of the color produced in this assay in a set of samples allows an assignment of the relative amounts of aziridine comprised by the coatings of those samples.

Similarly, where a second layer is applied onto the aziridine first layer, the second layer may be determined by another stain. In the case where the second layer is hyaluronan, an Alcian blue stain may be used to detect the presence of the hyaluronan layer.

The second layer may also be derived from exposing the aziridine layer to blood which in turn affects the immobilization of serum blood proteins to the surface and renders the surface passive to platelet activation.

The invention and its various embodiments will become more apparent from the following examples, which further illustrate preferred embodiments thereof.

EXAMPLE I

Synthesis of 2-(1-Aziridinyl) Ethyl Methacrylate

Under a nitrogen atmosphere, 14.4 mL of aziridineethanol (0.18 mole) and 30 mL of anhydrous dimethylformamide were placed into a dry 500 mL flask. To this there was added 75.3 mL of triethylamine (0.54 mole) and the mixture was stirred on ice for 30 minutes. To this mixture there was added dropwise 22.3 mL methacrylic anhydride (0.15 mole) and this was then stirred at room temperature overnight. The contents of the flask were then poured into a separatory funnel and the product was extracted with dichloromethane from sodium bicarbonate-saturated water twice and from brine once. The solvent was removed in vacuo and the desired product was purified by distillation and collected at 50° C. at 0.1 mm of Hg. 2-(1-Aziridinyl) ethyl methacrylate, 7.0 g (0.045 mole) was obtained (30% yield) as a colorless oil having the following analysis:

$^1$H NMR (400 MHz, CDCl$_3$); $\delta$=1.19(t, J=20 Hz, 2H, CH)$_2$, 1.79(t, J=20 Hz, 2H, CH), 1.96(s, 3H, CH$_2$), 2.50(t, J=5.6 Hz, 2H, CH$_2$), 4.32(t, J=5.6 Hz, 2H, CH$_2$), 5.58(s, 1H, H alkene), 6.14(s, 1H, H alkene)ppm.

$^{13}$C NMR (100 MHz, CDCl$_3$); $\delta$=18.5; 27.4; 59.9; 64.7; 125.9; 136.4; 167.6 ppm.

IR: (KBr) 2986.00; 1717.48; 1633.56; 1454.54; 1295.10; 1166.43; 937.06 cm$^{-1}$.

EXAMPLE II

Preparation of Aziridine Films

A. Deposition

A plasma reactor was used for depositing the films. The plasma reactor has a 4" diameter×24" long cylindrical glass chamber with inlet and exit ports at either end for vapor flow and an additional port for measuring reactor pressure. Capacitance coupled electrodes formed by two 1" wide strips of brass were wrapped around the outside of the reactor and spaced 6" apart. The downstream electrode was electrically grounded. A radio frequency generator and impedance matching network were used to apply an oscillating potential of desired power (5-100 watts) and frequency (13.56 MHz) to the upstream electrode. Flowmeters for inert gases and precursor vapors are located and connected upstream of the reactor.

In this capacitively coupled plasma reactor, aziridine films were plasma deposited onto polyethylene terephthalate (PET) sheets within the reactor. To do so, solvent sonicated samples of the films were placed in the reactor and etched with oxygen to activate their surfaces. The 2-(1-Aziridinyl) ethyl methacrylate compound of Example I was warmed to 33-36° C., degassed and fed into the plasma reactor via a mass flow controller at a controlled rate of 20 sccm (200 mtorr). A radio frequency was applied at 80 w, 13.56 MHz for two minutes whereupon the deposition power was decreased to 30-35 watts for 5-8 minutes. A temperature of 33-36° C. for the 2-(1-Aziridinyl) ethyl methacrylate compound provided the mass flow controller with sufficient vapor to sustain a 20 sccm flow rate for the duration of the deposition plus a 5-10 minute post-deposition aziridine vapor quench. Following the quench, argon was flowed across the samples for 10 minutes at a rate of 4 sccm (100 mtorr) and the samples were then left under an argon environment until they were removed from the reactor. The thickness of the deposited aziridine film on the samples is most likely greater than 100 Å.

B. Aziridine Functionality

Several samples produced in Example IIA in 0.5×2.5 cm pieces and having an overall thickness of about 0.5 mm were soaked overnight in 0.1% rhodamine stain solution. The rhodamine stain solution contained 0.03M succinic acid and 0.12M NaCl, and was pH adjusted to 4.10 with 5N NaOH. The soaked samples were then rinsed in deionized water and dried. The color of the samples were then determined. An increased in the pink color that is exhibited by the samples correlates with an increased presence of functional aziridines on the surface of the samples. No pink color was observed in PET controls that do not have the plasma-deposited aziridine film.

C. Formation of Lipid Enriched Layer

Samples of the plasma-deposited aziridine film on PET from Example IIA were exposed for 3 hours to 10 ml of isopropyl alcohol (IPA) solution containing 0.278 g tetradecyl phosphonic acid ($C_{14}PO_4$). The samples were then rinsed with IPA to remove any unbound $C_{14}PO_4$. Contact angles of the rinsed samples were measured with a Rame-Hart contact angle goniometer manufactured by Advanced Surface Technologies in Billerica, Mass.

The contact angle of a first sample having an aziridine film exposed only to IPA is 69.7°+/−0.9° (n=3, 1σ). The contact angle of a second sample having an aziridine film exposed to a IPA/$C_{14}PO_4$ solution is 88.4°+/−0.8° (n=3, 1σ). The increased contact angle of the second sample indicates that the hydrophobic chains of the tetradecyl phosphonic acid ($C_{14}PO_4$) were present on the sample surface.

X-ray Photoelectron Spectroscopy (XPS) analysis of the second sample indicated the incorporation of 2.8% phosphorus, an increase in carbon content and a decrease in nitrogen content in the outermost 100 Å of the surface. Consistent with the measurement of contact angle, the XPS analysis indicated that the alkyl phosphonic acid had been incorporated into the surface of the second sample.

EXAMPLE III

Drug Binding and Release

Samples of the aziridine deposited film and samples of PET as controls were soaked in 0.5M of Tranilast in 1-methyl-2-pyrrolidinone (NMP) solution for five days at room temperature. It was anticipated that the carboxylic acid group of Tranilast would react with the aziridine ring present in the plasma deposited film to form ester bonds. The presence of such ester bonds was determined by measuring the Tranilast release at two pH levels since the hydrolysis rate of ester bonds is slow in neutral solutions, but increases under either more basic or more acidic conditions. Samples of the aziridine deposited film and PET controls were soaked in 0.85% saline (at pH 6.0) and in saline plus 0.3 mM HEPES buffer (at pH 9.7). At intervals of 2, 4, 6 and 8 days, the samples were transferred to fresh saline solution of the appropriate pH and the absorbance measured at 340 nm to determine the concentration of Tranilast in the solution.

It was found that the initial burst of Tranilast release was greater from the PET controls than from the aziridine films. After the initial burst release from the PET samples, no additional Tranilast release was detected. However, Tranilast continued to be released from the aziridine film samples for 3-7 days. These findings indicate that the Tranilast release rate was greater at pH 9.7 than at pH 6.0 and that the Tranilast was bound to the aziridine ring via ester linkages. FIG. 1 summarizes the observed release of the Tranilast from various samples at pH 6.0 and 9.7.

EXAMPLE IV

Hyaluronic Acid Binding

A set of plasma-deposited aziridine films on PET samples from Example IIA in 1 cm×2.5 cm pieces were exposed to a 0.1 w % of 1 MDa hyaluronic acid (HA) solution at room temperature. The HA solution was buffered at pH 4.11 with 0.03M succinate buffer. The samples were then soaked for 2 hours in phosphate buffer saline (PBS) at 37° C. to remove weakly bound HA, then stained for 10 seconds with 1% Alcian blue, and rinsed in deionized water.

The samples exposed to the Alcian blue stain developed a faint blue color, indicating the presence of a thin HA layer. A control sample of plasma-deposited aziridine film on PET that was not exposed to an HA solution failed to stain with Alcian blue indicating that the stain did not bind nonspecifically to the aziridine film. The blue color did not fade from the samples of the Alcian blue stained HA-aziridine film after soaking overnight in 8M urea or 4M NaCl.

These results indicate that an extremely thin layer of HA was bound to the surfaces of the aziridine film samples in such a manner that it could not be removed by disruption of hydrophobic or static attractive forces. Such HA thin layers would be useful in preventing thrombus formation on blood contacting devices.

EXAMPLE V

Cell Adhesion from Platelet Rich Plasma

Plasma-deposited aziridine film on PET samples were examined for their resistance to cell adhesion.

Plasma-deposited aziridine film on PET samples that were made as described in Example IIA were exposed overnight at room temperature to a 0.1 w % solution of 1 MDa HA buffered at pH 4.11 with a 0.03 M succinate buffer. The exposed samples were then soaked for 1 hour in phosphate buffer saline (PBS) at 37° C. and then rinsed with a large volume of reverse osmosis purified water.

The controls that were used were PET samples and plasma-deposited aziridine film samples untreated with HA. All of the samples and the controls were exposed to platelet rich plasma for 20 min. at room temperature, rinsed with PBS, fixed with 3.7% formaldehyde, stained for 90 minutes with 1% Coomassie blue, destained with 5% acetic acid and photographed under 100× magnification. Presence of cells is indicated by the color of the Coomassie blue stain that attaches on the cells.

The results obtained showed that cells adhered to the PET controls, but adhered to only two of the twelve HA-treated aziridine films prepared under a range of conditions. It was also observed that cells attached to scratches made on PET samples that had been coated with HA-treated aziridine films. These scratches were intentionally made as internal controls prior to the exposure of the films to the platelet rich plasma. These results indicate that a wide range of HA-treated aziridine films are capable of resisting cell adhesion from platelet rich plasma.

Additionally, cells were observed not to adhere to the control aziridine film samples untreated with HA when exposed to the platelet rich plasma. This indicates that the aziridine film may absorb a layer of benign proteins such as, for example, serum albumin that inhibit platelet adhesion.

In further experiments, the plasma deposition was varied by placing the PET substrate in three different locations in the plasma reactor: upstream from, between, and downstream from the active electrodes. The plasma treated PET substrates from each of these locations were subsequently exposed to a 0.1 w % solution of 1 MDa HA as described above. It appeared that all the PET substrates that have been plasma treated and exposed to the HA solution were resistant to cell adhesion when exposed to platelet rich plasma, irrespective of the location the PET substrate was placed in the plasma reactor.

Although the invention has been described with particularity and in some detail, it will be appreciated by those skilled in this art that changes and modifications can be made therein without departing from the scope and spirit of the invention. Specifically, polysaccharides other than HA may be used to bind with the aziridine films. These polysaccharides include heparin, alginate, carboxylmethyl cellulose and dextran sulfate.

The invention is not limited by the embodiments described above which are presented as examples only but can be modified in various ways within the scope of protection defined by the appended patent claims.

Thus, while there have shown and described and pointed out fundamental novel features of the invention as applied to a preferred embodiment thereof, it will be understood that various omissions and substitutions and changes in the form and details of the processes, devices and articles illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

References cited herein are incorporated by reference in their entirety.

We claim:

1. A process of producing a coated surface on a substrate, comprising
   a) providing a substrate; and
   b) plasma depositing an aziridine compound onto the substrate to produce at least one aziridine-coated surface on the substrate, wherein the aziridine compound has a functional group that is linked to the aziridine and that is susceptible to fragmentation and recombination, with the proviso that the functional group is not a silane or a siloxane, and, if the nitrogen atom of the aziridine is attached to hydrogen, then an alkyl pendent to the carbon of the aziridine has 4 or more carbon atoms.

2. The process of claim 1 wherein the aziridine compound has at least one functional group selected from the group consisting of allyl, alkoxy, alkylene, aryl, ester, ether, ethylene glycol, oligoethylene glycol, and acryl.

3. The process of claim 1 wherein the aziridine compound has an alkylene group.

4. The process of claim 3 wherein the aziridine compound has an acryl group.

5. The process of claim 4 wherein the aziridine compound has a molecular weight of 600 or less.

6. The process of claim 4 wherein the aziridine is linked to the acryl group by a linker selected from the group consisting of alkyl, alkylene, alkylene oxide, alkyl diols, and combinations thereof.

7. The process of claim 6 wherein the linker is polypropylene oxide.

8. The process of claim 6 wherein the linker is polyethylene glycol.

9. The process of claim 6 wherein the linker comprises polyethylene glycol and polypropylene oxide.

10. The process of claim 1 wherein the aziridine compound is

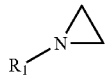

(I)

wherein $R_1$ is selected from the group consisting of a substituted or unsubstituted alkyl, alkoxy, alkenyl, alkinyl, aryl, arylalkyl, cycloalkylalkyl, cycloalkenyl, heterocyclic, heteroaryl, heteroarylalkyl, acrylate, alkylacrylate, alkylacrylate esters, alkylester, alkylether, alkylcarbonyl, fluorocarbon, ethylene glycol, oligo ethylene glycol groups, and combinations thereof.

11. The process of claim 10, wherein the substitution group is selected from the group consisting of a halogen, $C_1$-$C_{22}$ alkyl, nitro, cyano, aryl, thiol, cycloalkyl, fluorocarbon, ethylene glycol, oligoethylene glycol and heterocyclic groups.

12. The process of claim 1 wherein the aziridine compound is

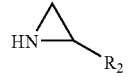

(II)

wherein $R_2$ is selected from the group consisting of a substituted or unsubstituted alkyl having 4 or more carbon atoms, alkoxy, alkenyl, alkinyl, aryl, arylalkyl, cycloalkylalkyl, cycloalkenyl, heterocyclic, heteroaryl, heteroarylalkyl, acrylate, alkylacrylate, alkylacrylate esters, alkylester, alkylether, alkylcarbonyl, fluorocarbon, ethylene glycol, oligo ethylene glycol groups, and combinations thereof.

13. The process of claim 12, wherein the substitution group is selected from the group consisting of a halogen, $C_1$-$C_{22}$ alkyl, nitro, cyano, aryl, thiol, cycloalkyl, fluorocarbon, ethylene glycol, oligoethylene glycol and heterocyclic groups.

14. The process of claim 1 wherein the aziridine compound is

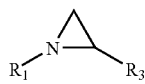

wherein R₁ and R₃ are selected from the group consisting of a substituted or unsubstituted alkyl, alkoxy, alkenyl, alkinyl, aryl, arylalkyl, cycloalkylalkyl, cycloalkenyl, heterocyclic, heteroaryl, heteroarylalkyl, acrylate, alkylacrylate, alkylacrylate esters, alkylester, alkylether, alkylcarbonyl, fluorocarbon, ethylene glycol, oligo ethylene glycol groups, and combinations thereof.

15. The process of claim 14, wherein the substitution group is selected from the group consisting of a halogen, $C_1$-$C_{22}$ alkyl, nitro, cyano, aryl, thiol, cycloalkyl, fluorocarbon, ethylene glycol, oligoethylene glycol and heterocyclic groups.

16. The process of claim 4 wherein the aziridine compound is 2-(1-aziridinyl) ethyl methacrylate.

17. The process of claim 1 wherein the substrate is selected from the group consisting of polyethylene terephthalate, polycarbonate, polymethacrylate, silicone, polytetrafluoroethylene, polyurethanes, polybutadienes, epoxies, polystyrenes, polybutyrates, hydroxy apatites, ceramics, glass, and metals.

18. The process of claim 1 wherein the substrate is etched with oxygen before plasma depositing the aziridine compound.

19. The process of claim 1 further comprising the step of coating the aziridine coated surface with a biopolymer.

20. The process of claim 19 wherein the biopolymer is selected from the group consisting of protein, heparin complex, polysaccharide, phosphonic acid, and nucleic acid.

21. The process of claim 20 wherein the polysaccharide is hyaluronan, alginate, or carboxymethyl cellulose.

22. The process of claim 20 wherein the protein is collagen, laminin or albumin.

23. The process of claim 20 wherein the nucleic acid is DNA, RNA or antisense material.

24. A coated substrate produced by the process of claim 1.

25. A coated substrate produced by the process of claim 16.

26. A coated substrate produced by the process of claim 19.

27. A device comprising:
(a) a substrate; and
(b) a film on said substrate, wherein said film is plasma deposited with an aziridine compound, wherein the aziridine compound has a functional group that is linked to the aziridine and that is susceptible to fragmentation and recombination, and with the proviso that the functional group is not a silane or a siloxane, and, if the nitrogen atom of the aziridine is attached to hydrogen, then an alkyl pendent to the carbon of the aziridine has 4 or more carbon atoms.

28. The device of claim 27 wherein the aziridine compound has at least one other functional group selected from the group consisting of allyl, alkoxy, alkylene, aryl, ester, ether, ethylene glycol, oligoethylene glycol, and acryl.

29. The device of claim 28 wherein the aziridine compound has an alkylene group.

30. The device of claim 28 wherein the aziridine compound has an acryl group.

31. The device of claim 27 wherein the aziridine compound has a molecular weight of 600 or less.

32. The device of claim 27 wherein the aziridine is linked to the acryl group by a linker selected from the group consisting of alkyl, alkylene, alkylene oxide, alkyl diols and combinations there.

33. The device of claim 32 wherein the linker is polypropylene oxide.

34. The device of claim 32 wherein the linker is polyethylene glycol.

35. The device of claim 32 wherein the linker comprises polyethylene glycol and polypropylene oxide.

36. The device of claim 27 wherein the aziridine compound is

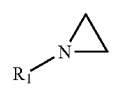

wherein R₁ is selected from the group consisting of a substituted or unsubstituted alkyl, alkoxy, alkenyl, alkinyl, aryl, arylalkyl cycloalkylalkyl, cycloalkenyl, heterocyclic, heteroaryl, heteroarylalkyl, acrylate, alkylacrylate, alkylacrylate esters, alkylester, alkylether, alkylcarbonyl, fluorocarbon, ethylene glycol, oligo ethylene glycol groups, and a combination thereof.

37. The device of claim 27, wherein the substitution group is selected from the group consisting of a halogen, $C_1$-$C_{22}$ alkyl, nitro, cyano, aryl, thiol, cycloalkyl, fluorocarbon, ethylene glycol, oligoethylene glycol and heterocyclic groups.

38. The device of claim 27 wherein the aziridine compound is

wherein R₂ is selected from the group consisting of a substituted or unsubstituted alkyl having 4 or more carbon atoms, alkoxy, alkenyl, alkinyl, aryl, arylalkyl cycloalkylalkyl, cycloalkenyl, heterocyclic, heteroaryl, heteroarylalkyl, acrylate, alkylacrylate, alkylacrylate esters, alkylester, alkylether, alkylcarbonyl, fluorocarbon, ethylene glycol, oligo ethylene glycol groups, and a combination thereof.

39. The device of claim 38, wherein the substitution group is selected from the group consisting of a halogen, $C_1$-$C_{22}$ alkyl, nitro, cyano, aryl, thiol, cycloalkyl, fluorocarbon, ethylene glycol, oligoethylene glycol and heterocyclic groups.

40. The device of claim 27 wherein the aziridine compound is

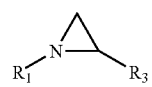

wherein R₁ and R₃ are selected from the group consisting of a substituted or unsubstituted alkyl, alkoxy, alkenyl, alkinyl, aryl, arylalkyl cycloalkylalkyl, cycloalkenyl, heterocyclic, heteroaryl, heteroarylalkyl, acrylate, alkylacrylate, alkylacrylate esters, alkylester, alkylether, alkylcarbonyl, fluorocarbon, ethylene glycol, oligo ethylene glycol groups, and a combination thereof.

41. The device of claim 40, wherein the substitution group is selected from the group consisting of a halogen, $C_1$-$C_{22}$ alkyl, nitro, cyano, aryl, thiol, cycloalkyl, fluorocarbon, ethylene glycol, oligoethylene glycol and heterocyclic groups.

42. The device of claim 27 wherein the aziridine compound is 2-(1-aziridinyl) ethyl methacrylate.

43. The device of claim 27 further comprising a pharmaceutical or therapeutic agent immobilized onto said film.

44. The device of claim 43 wherein said pharmaceutical or therapeutic agent is a member selected from the group consisting of anti-allergenics, anti-bacterials, anti-virals, anti-fungals, anti-inflammatories, antiplatelets, antithrombotics, anesthetics, anti-proliferatives, genetic materials and mixtures thereof.

45. The device of claim 44 wherein the genetic materials are selected from the group consisting of DNA, RNA and antisense material.

46. The device of claim 27 wherein the film is covered by a biopolymer layer.

47. The device of claim 46 wherein the biopolymer is selected from the group consisting of protein, heparin complex, polysaccharide, phosphonic acid, and nucleic acid.

48. The device of claim 47 wherein the polysaccharide is hyaluronan.

49. The device of claim 46 wherein a pharmaceutical or therapeutic agent immobilized onto said biopolymer layer.

50. A method of preventing cell adhesion on a substrate comprising the plasma deposition of aziridine on the substrate to form an aziridine film, wherein the aziridine compound has a functional group that is linked to the aziridine and that is susceptible to fragmentation and recombination, and with the proviso that the functional group is not a silane or a siloxane, and, if the nitrogen atom of the aziridine is attached to hydrogen, then an alkyl pendant to the carbon of the aziridine has 4 or more carbon atoms.

51. The method of claim 50, further comprising the application of a biopolymer layer on the aziridine film.

52. The method of claim 51 wherein the biopolymer is selected from the group consisting of protein, heparin complex, polysaccharide, phosphonic acid, and nucleic acid.

* * * * *

UNITED STATES PATENT AND TRADEMARK OFFICE
CERTIFICATE OF CORRECTION

| | |
|---|---|
| PATENT NO. | : 7,387,836 B2 |
| APPLICATION NO. | : 10/511425 |
| DATED | : June 17, 2008 |
| INVENTOR(S) | : Diego A. Gianolio |

It is certified that error appears in the above-identified patent and that said Letters Patent is hereby corrected as shown below:

On the Title Page, insert

--Related U.S. Application Data:

(60) Provisional Application No. 60/373,136, filed on April 17, 2002.--

Signed and Sealed this

Tenth Day of March, 2009

JOHN DOLL
*Acting Director of the United States Patent and Trademark Office*